United States Patent [19]

Kennedy et al.

[11] Patent Number: 5,095,273

[45] Date of Patent: Mar. 10, 1992

[54] METHOD FOR DETERMINING TENSOR CONDUCTIVITY COMPONENTS OF A TRANSVERSELY ISOTROPIC CORE SAMPLE OF A SUBTERRANEAN FORMATION

[75] Inventors: W. David Kennedy, Carrollton; Wyatt W. Givens, Dallas, both of Tex.

[73] Assignee: Mobil Oil Corporation, Fairfax, Va.

[21] Appl. No.: 671,248

[22] Filed: Mar. 19, 1991

[51] Int. Cl.$^5$ .......................... G01V 3/02; E21B 49/02
[52] U.S. Cl. ...................................... 324/376; 73/153
[58] Field of Search ........................ 324/376, 446, 449; 73/153

[56] References Cited

U.S. PATENT DOCUMENTS

| | | | |
|---|---|---|---|
| 2,613,250 | 10/1952 | Bilhartz et al. | 324/376 X |
| 2,745,057 | 5/1956 | Dotson | 324/376 |
| 2,802,172 | 8/1957 | Mueller et al. | 324/376 |
| 3,243,695 | 3/1966 | Roark et al. | 324/376 |
| 3,839,899 | 10/1974 | McMillen | 73/38 |
| 4,379,407 | 4/1983 | Masse et al. | 73/579 |
| 4,467,642 | 8/1984 | Givens | 73/152 |
| 4,546,318 | 10/1985 | Bowden | 324/376 |
| 4,686,477 | 8/1987 | Givens et al. | 324/366 |
| 4,688,238 | 8/1987 | Sprunt et al. | 378/4 |
| 4,907,448 | 3/1990 | Givens | 73/153 |
| 4,924,187 | 5/1990 | Sprunt et al. | 324/376 |
| 4,926,128 | 5/1990 | Givens | 324/376 |

*Primary Examiner*—Gerard R. Strecker
*Attorney, Agent, or Firm*—Alexander J. McKillop; Charles J. Speciale; George W. Hager, Jr.

[57] ABSTRACT

A transversely isotropic cylindrical core sample of a subterranean formation is fluid saturated and subjected to a confining pressure. Electrical potential is measured along the core sample and in a plurality of direction through the core sample which are normal to the cylindrical axis of the core sample at a plurality of spaced-apart positions along such axis. From these electric potential measurement tensor conductivity components normal to and lying within the bedding plane of the core sample are determined.

9 Claims, 3 Drawing Sheets

METHOD FOR DETERMINING TENSOR CONDUCTIVITY COMPONENTS OF A TRANSVERSELY ISOTROPIC CORE SAMPLE OF A SUBTERRANEAN FORMATION

BACKGROUND OF THE INVENTION

This invention relates to the area of oil and natural gas exploration and, more particularly, to a method for identifying regions of rock formations from which hydrocarbons may be produced.

Hydrocarbon saturation $S_O$ is generally determined from a measured water saturation $S_W$ as follows:

$$S_O = 1 - S_W \qquad (1)$$

Water saturation present in a subterranean formation is typically determined from interpretation of conventional electrical (i.e., resistivity) logs recorded in a borehole drilled through the formation. Water saturation of the available pore space of the formation is determined from the resistivity log measurements using the Archie equation se forth in "The Electrical Resistivity Log As An Aid In Determining Some Reservoir Characteristics", Trans. AIME, Vol. 46, pp. 54–62, 1942, by G. E. Archie. This equation is expressed as $$S_w{}^n = R_w / \phi^M R_t \qquad (2)$$

where $S_w$ is the fractional water saturation (i.e. free and bound water of the formation expressed as a percent of the available pore space of the formation), $R_w$ is the formation water resistivity, $\phi$ is the formation porosity, $R_t$ is the formation electrical resistivity, n is the saturation exponent and m is the porosity or cementation exponent. The Archie equation may be expressed in other ways and there are numerous methods in the art for determining, measuring or otherwise obtaining the various components needed to predict fractional water saturation $S_w$ from the formation resistivity, $R_t$, using the equation in any of its forms.

Certain logs have provided formation resistivity $R_t$ and porosity $\phi$. Water samples provide the best values for $R_w$. Standard practice is to measure rock sample resistivities $R_o$ and $R_t$ for a number of water saturations and to plot the logarithm of I versus the logarithm of $S_w$. Archie's equations assume such a logarithmic plot can be fit by a straight line with slope of $-n$.

When the physical properties of a core sample from a subterranean formation are isotropic, the formation resistivity $R_t$ measurement gives the same value regardless of how the core sample is oriented with respect to the larger rock sample from which such sample is obtained. Many core samples are, however, not homogenous and electrically isotropic and resistivity (or its reciprocal, conductivity) is not isotropic, but has different values according to the direction in which the core sample was taken. A conductivity computed from the sampled voltage and injected current multiplied by a geometrical factor gives a conductivity value which is a mixture of the conductivities in three orthogonal directions in the core sample. However, a commonly encountered form of an anisotropic medium in an earth formation is termed transversely isotropic having only two distinct values of conductivity. When sedimentary layers are visible, it can be assumed that conductivity in any direction parallel to the layering has a uniform value, while conductivity perpendicular to the layering has a different value. Conductivities measured in any other directions will exhibit a mixture of these two values. For such anisotropic core samples, the Archie saturation exponent n is strongly dependent on the direction the conductivity measurement is made and when such measurement is taken across permeability barriers within the core sample the saturation exponent may be one and a half times as large as if the measurements were taken parallel to the permeability barriers. This difference can have a large detrimental effect on the determination of hydrocarbon reserves derived from the calculated water saturation of equation (2). Previous methods for carrying out such measurements have required the use of a pair of cylindrical core samples or a single cubic core sample. Firstly, for the pair of cylindrical core samples, one is cut parallel to the bedding plane and the other is cut perpendicular to the bedding plane. Two difficulties are inherent; one is that the pair of core samples may not be identical in all respects except for the direction of the planes relative to the cylindrical axes of the core samples, and the other is that it would be extremely difficult to obtain the same partial water saturations in each core sample for comparison measurements. Secondly, for the single cubic core sample, the sample is cut with the bedding plane parallel to two faces of the cube and normal to two faces of the cube. This makes it difficult to carry out conductivity measurements at in-situ pressure.

It is, therefore, an object of the present invention to determine the tensor components of conductivity of a single cylindrical core sample that is electrically anisotropic and to identify the degree of anisotropy changes as the brine saturation of the core sample changes so that an accurate water saturation can be calculated from equation (2).

SUMMARY OF THE INVENTION

The present invention is directed to a method for measuring conductivity of a transversely isotropic core sample from a subterranean formation.

The core sample is shaped in the form of a cylinder having its cylindrical axis at an angle to the bedding plane of the subterranean formation comprising the core sample and having a confining pressure applied. Electric potential, or voltage, is measured along the core sample and in a plurality of directions through the core sample which are normal to the cylindrical axis of the core sample at a plurality of spaced-apart positions along such axis. From these voltage measurements tensor conductivity components are determined. Any electrical anisotropy in the core sample can be identified based on comparison of tensor conductivity components.

In carrying out the voltage measurements, the outer surface of the core sample is contacted with an array of electrodes at each of a plurality of spaced-apart positions along the length of the core sample, each of the arrays being in a plane normal to the axis and the electrodes in each of the arrays being equally spaced at an even number of positions about the outer surface of the core sample. A voltage is measured along the axial length of the core sample and across each pair of electrodes that are spaced 180° apart about the core sample. The voltage measurements are utilized to determine conductivity along the core sample and in radial directions through the core sample normal to the axis between each pair of electrodes. Tensor conductivity components both normal to the bedding plane of the core sample and lying within the bedding plane of the core sample are determined from the voltage measurements.

In a further aspect, an initial fluid saturation is established within the core sample and the conductivities determined. The fluid saturation is then altered a plurality of times and the conductivities determined for each of such differing fluid saturations. The conductivities thus determined may then be used to obtain Archie exponents m and n which are directionally dependent.

DESCRIPTION OF THE PREFERRED EMBODIMENT

Figure 1:
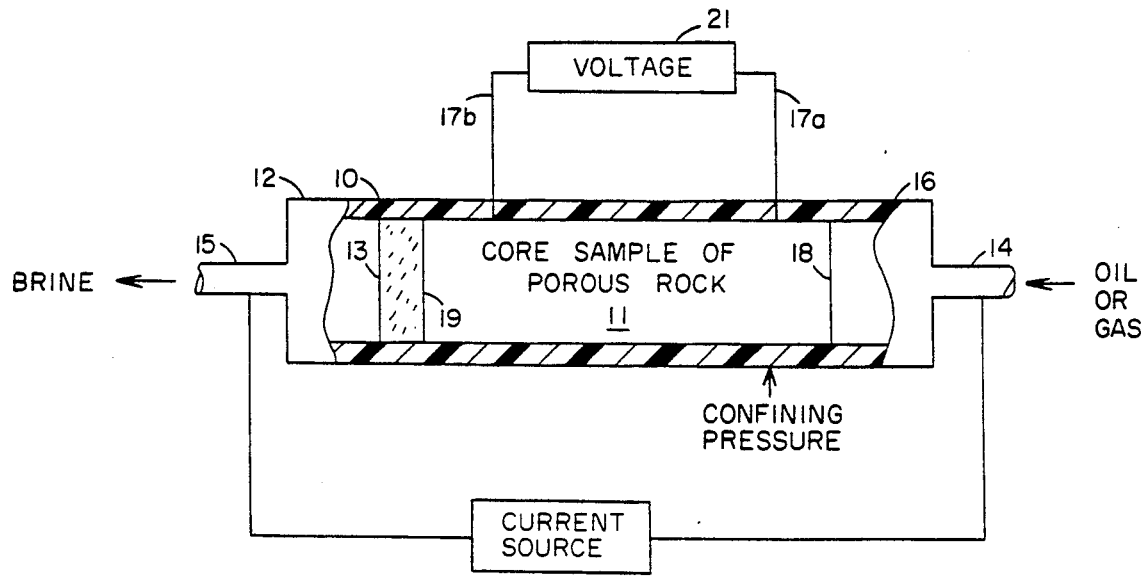
FIG. 1 illustrates prior art apparatus for carrying out resistivity measurements on core samples of subterranean formations.

A system that has been successfully used in carrying out linear resistivity measurements along a core sample from a subterranean formation is shown in FIG. 1 (prior art). A pressure sleeve 10, preferably natural or synthetic rubber, surrounds a cylindrical core sample 11 of a porous rock to be measured for resistivity at a plurality of fluid saturations. Positioned between the core sample 11 and end 12 of the pressure sleeve 10 is a porous member 13, which is permeable to a first fluid saturating the core sample, but is impermeable to a second fluid used to displace the first fluid from the core sample. The second, or displacing fluid, is immiscible with the first fluid saturating the core sample and is of different electrical conductivity. This first saturation fluid is the wetting fluid for the porous member 13, which by way of example, may be a ceramic plate or a membrane. Sleeve 10 is placed inside a suitable pressure vessel (not shown) that can be pressurized up to several thousand pounds per square inch. Typical of such pressure vessels are those described in U.S. Pat. Nos. 3,839,899 to McMillan; 4,688,238 to Sprunt et al; and 4,379,407 to Masse et al., the teachings of which are incorporated herein by reference. Through such a pressure vessel a pressure is applied to the sleeve 10 and hence to the porous rock 11. The pressure should be sufficient to eliminate any fluid annulus between the sleeve and the surface of the core sample. A fluid inlet 14 and a fluid outlet 15 feed into the ends 16 and 12 respectively of the sleeve 10. Both inlet 14 and outlet 15 also serve as current conducting electrodes for passing current from a source 20 through the porous rock 11. A pair of voltage electrodes 17a and 17b penetrate sleeve 10 and make contact with the porous rock at spaced locations along the length of the porous rock. The voltage across the porous rock 11 between the electrodes 17a and 17b is measured by the unit 21.

The core sample of porous rock 11 is initially fully saturated, by way of example, with an electrically conducting fluid, such as salt water, and placed under confining pressure. A current is passed through the porous rock and a voltage along the length of the porous rock is measured between electrodes 17a and 17b. Such voltage measurements may be carried out in accordance with the teachings of U.S. Pat. Nos. 4,467,642 to Givens; 4,546,318 to Bowden and 4,686,477 to Givens et al, the teachings of which are incorporated herein by reference. The resistivity (or its reciprocal, conductivity) of the porous rock is determined using the measured voltage, the length, and the cross-sectional area of the core. A displacing fluid such as a nonconducting oil or gas, may then be forced through inlet 14 into end 18 of porous rock 11 to change the fluid saturation condition prior to the making of the next resistivity measurement.

Typical of such a resistivity measuring system of FIG. 1 are those described in U.S. Pat. Nos. 4,907,448 and 4,926,128 to Givens and 4,924,187 to Sprunt et al.

Having now described a typical resistivity measurement carried out in a single direction along the axial direction of a cylindrical core sample as shown in FIG. 1, the present invention of providing tensor components of conductivity needed for interpreting electric logs of a subterranean formation with anisotropic properties by measuring and comparing conductivity in a plurality of radial directions through a cylindrical core sample of the formation and normal to its cylindrical axis will now be described. A transversely isotropic cylindrical core sample of the formation is cut so that the formation bedding plane is at an angle to the cylindrical axis of the core sample. The core sample is initially saturated with an electrically conducting fluid such as salt water, and placed within sleeve 10 under confining pressure representative of in-situ pressure. The core sample is contacted with an array of electrodes contained by sleeve 10 at each of a plurality of spaced-apart positions along the length of the core sample, such as electrode arrays A, B and C of FIG. 2 for example. Each such array A-C lies in a plane normal to the axis of the core sample and the electrodes in each array are equally spaced at an even number of positions about the sleeve 10.

Figure 2:
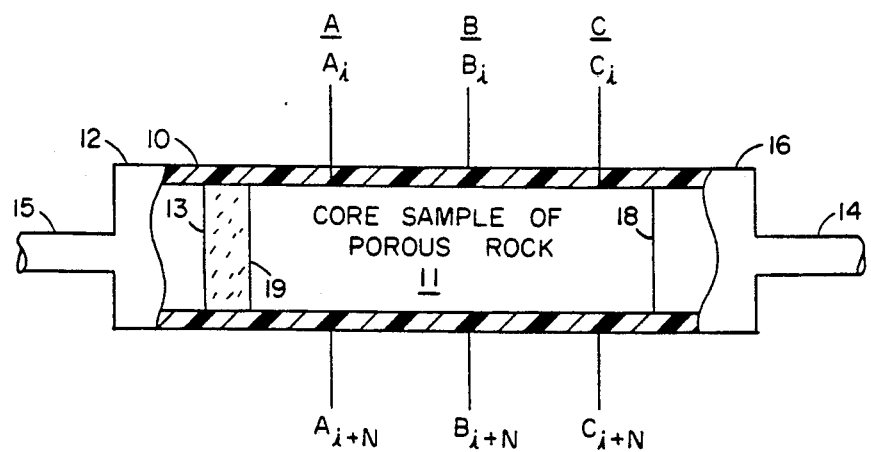
FIG. 2 illustrates apparatus employing electrode arrays for carrying out conductivity measurements on a transversely isotropic core sample of subterranean formations in accordance with the present invention.
Figure 3:
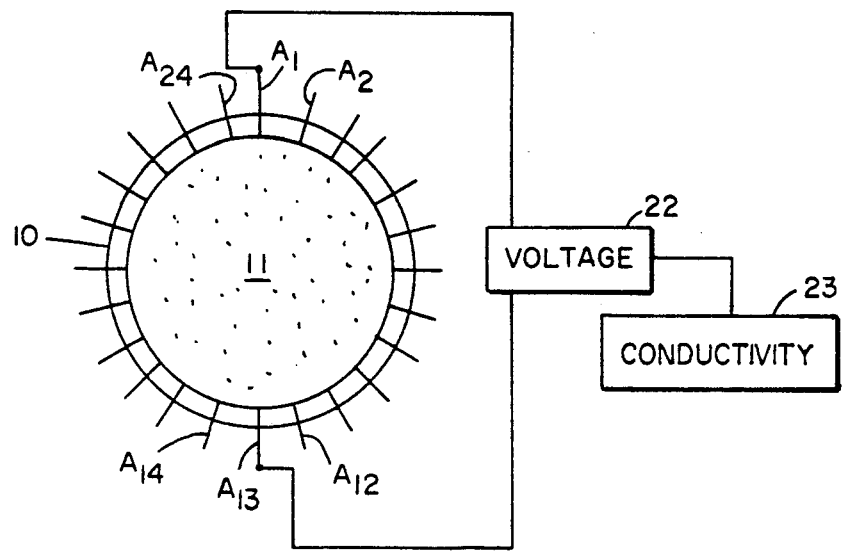
FIG. 3 is a cross-sectional view through the apparatus of FIG. 2 showing in detail one of the electrode arrays of FIG. 2.

FIG. 2 shows a pair of such electrodes $A_i$ and $A_{i+N}$ which are spaced-apart 180° about sleeve 10 (with i=1 to N). FIG. 3 is a cross-sectional view taken through the sleeve 10 and core sample 11 at the axial position of array A with 24 electrodes $A_1$-$A_{24}$ being shown (cross-sectioning of sleeve 10 being omitted for clarity). As can be seen in FIG. 3 there are 12 electrode pairs at 180° spaced-apart positions about sleeve 10 such as electrode pairs $A_1$ and $A_{13}$, $A_2$ and $A_{14}$—$A_{12}$ and $A_{24}$. A current is passed through core sample 11 and a voltage is measured across each of the $A_i$ and $A_{i+N}$, $B_i$ and $B_{i+N}$, and $C_i$ and $C_{i+N}$ electrode pairs spaced-apart 180° about the arrays A, B and C such as shown by voltage unit 22 across electrode pair $A_1$-$A_{13}$ for example. These voltages as well as a voltage measured along the axial length of the core sample by unit 21, such as shown in FIG. 1, are used by a conductivity unit 23 to determine the conductivities of the core sample both along the core sample and in the plurality of radial directions through the core sample normal to core sample axis between the electrodes of each corresponding electrode pair. Following these measurements, the fluid saturation in the core sample may be altered any number of times with such measurements being repeated for each differing fluid saturation.

From these conductivities along and normal to the axis of the core sample at a plurality of positions along the axis of the core sample the desired tensor components of conductivity needed for interpreting electric logs of subterranean formations with anisotropic properties are determined. Core samples cut parallel and perpendicular to visible bedding planes at neighboring locations might be used to indicate and measure electrical anisotropy. However, such a procedure cannot be definitive because the samples might differ in their electrical properties regardless of how close together they resided in the original rock, and it would be difficult to obtain the same partial water saturations in each core sample for comparison measurements. A single cylindrical core sample cut with the bedding plane at an angle to the axis of the core sample as described above is utilized in accordance with the present invention to overcome such limitations.

Figure 4:
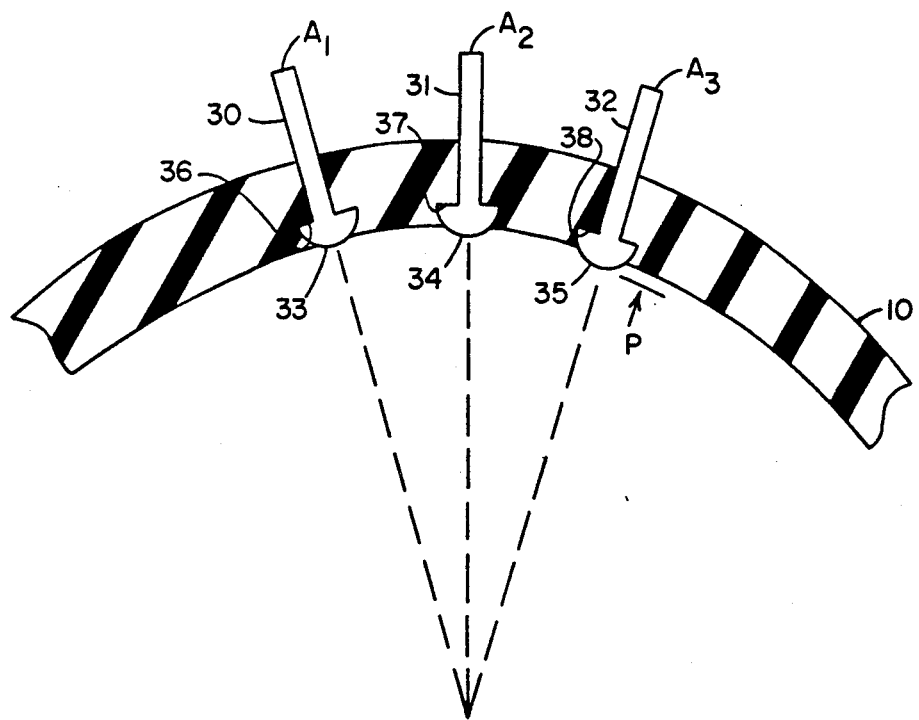
FIG. 4 illustrates one configuration for the electrodes of each of the electrode arrays of FIGS. 2 and 3.

Referring now to FIG. 4, there is shown a preferred configuration for the electrodes of each of the electrode arrays A-C. For purpose of example, electrodes $A_1$-$A_3$ are shown molded into a rubber sleeve 10 with cylindrical main body members 30-32 and spherical-like end members 33-35 for making contact with the outer surface of a core sample by extending outward from the inner surface of sleeve 10 by a distance P. As shown in FIG. 4, end members 33-35 are semispherical with recessed portions, or lips, 36-38, being normal to the outer surface of the cylindrical main body members 30-32. Such a semispherical end member provides for enhanced adhesion to the rubber sleeve 10.

Having described apparatus for carrying out the desired conductivity measurements for use in the determination of tensor conductivity components within a core sample, the method of utilizing such determined tensor conductivity components to identify electrical anisotrophy will now be described.

A commonly encountered type of anisotropic medium in earth formations is termed transversely isotropic. Such a medium has only two distinct values of conductivity. In formations having visible bedding layers, it can be assumed that conductivity in any direction parallel to the bedding layers has a uniform value, while conductivity perpendicular to the layers has, in general, a different value. Conductivities measured in other directions exhibit a mixture of these two values. In accordance with the present invention, a core sample having visible bedding planes and transversely isotropic conductivity is utilized to obtain the principle components of the conductivity tensor, that is, the component normal to the bedding plane and the component lying is the bedding plane.

In linear media, electric current density is related to electric field through the constitutive relation $$\bar{J} = \bar{\bar{\sigma}} \bar{E} \quad (3)$$

where $\bar{J}$ and $\bar{E}$ are vector fields and $\sigma$ is the conductivity tensor. In general the current density and electric field need not be in the same direction.

Considering a transversely isotropic conductivity structure such that the plane of symmetry of conductivity is parallel to visible bedding planes in the core sample, the axes of the conductivity tensor are assigned such that $$\sigma_{xx} = \sigma_{yy} \neq \sigma_{zz} \quad (4)$$

In a coordinate system conformable with the principal axes of the conductivity tensor, the tensor takes a diagonal form. Thus $$\bar{J} = \bar{\bar{\sigma}}' \bar{E} \rightarrow \begin{bmatrix} J_x' \\ J_y' \\ J_z' \end{bmatrix} = \begin{bmatrix} \sigma_{xx}' & 0 & 0 \\ 0 & \sigma_{yy}' & 0 \\ 0 & 0 & \sigma_{zz}' \end{bmatrix} \begin{bmatrix} E_x \\ E_y \\ E_z \end{bmatrix} \quad (5)$$

where the primes have been introduced to designate coordinates in the principal axis coordinate system.

Figure 5:
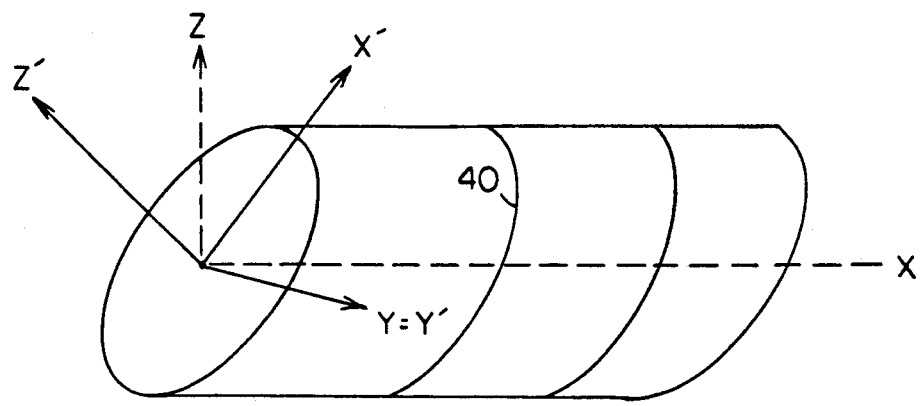
FIG. 5 illustrates the relationship of a coordinate system referenced to the axis of a core sample and another coordinate system referenced to bedding planes visible within a core sample. The y and y' axis are chosen to coincide.

Measurements are obtained from a core sample such as shown in FIG. 5 whose cylindrical, or longitudinal, axis is taken as the x axis in a reference frame referred to as the "laboratory" or "lab" frame. The y axis is a level line lying in one of the visible bedding planes, and the z axis is vertical. The core is assumed to be oriented so that the y axis in the core coincides with the y axis in the lab frame.

The relationship between the principal axis coordinate frame and the lab coordinate frame is schematically illustrated in FIG. 5. The core sample is sliced parallel to one of the bedding planes 40, for example, on its left face to facilitate the visualization of the axes. Axes x' and y' lie in the bedding plane. Axis z' is normal to the bedding plane. Axis y' is a level line coinciding with the semi-minor axis of the ellipse formed when the core sample is sliced. The y axis coincides with axis y', the x axis is the longitudinal axis of the core and the z axis is vertical.

There exists a linear transformation which carries J' into J, i.e., $$\bar{J} = \bar{\bar{T}} \bar{J}'. \quad (6)$$

The same transformation carries any vector in the primed space into its representation in the unprimed space. Thus $$\bar{E} = \bar{\bar{T}} \bar{E}'. \quad (7)$$

The corresponding form in the laboratory frame is derived from the simplest expression for the constitutive relation $$\bar{J}' = \bar{\bar{\sigma}}' \bar{E}'. \quad (8)$$

Multiplying by $\bar{\bar{T}}$ yields $$\bar{\bar{T}} \bar{J}' = \bar{\bar{T}} \bar{\bar{\sigma}}' \bar{E}'. \quad (9)$$

The transformation is unitary, i.e., $\bar{\bar{T}} \bar{\bar{T}}^{-1} = \bar{\bar{T}}^{-1} \bar{\bar{T}} = \bar{\bar{I}}$, where $\bar{\bar{I}}$ is the identity matrix and $\bar{\bar{T}}^{-1}$ is the inverse of $\bar{\bar{T}}$.

Thus $$\bar{\bar{T}} \bar{J}' = \bar{\bar{T}} \bar{\bar{\sigma}}' \bar{\bar{I}} \bar{E}' = \bar{\bar{T}} \bar{\bar{\sigma}}' \bar{\bar{T}}^{-1} \bar{\bar{T}} \bar{E}'. \quad (10)$$

Using $\bar{J} = \bar{\bar{T}} \bar{J}'$ from Equation 6, and $\bar{E} = \bar{\bar{T}} \bar{E}'$ from Equation 7, then $\bar{J} = \bar{\bar{T}} \bar{\bar{\sigma}}' \bar{\bar{T}}^{-1} \bar{E}$.

This relation expresses current density in the laboratory frame in terms of electric field in the laboratory frame. The tensor relating the fields is expressed in terms of the conductivity tensor in the principal axis frame and the transformations $\bar{\bar{T}}$ and $\bar{\bar{T}}^{-1}$.

From $\bar{\bar{\sigma}} = \bar{\bar{T}} \bar{\bar{\sigma}}' \bar{\bar{T}}^{-1}$ (11)

there is obtained the formal constituative relation in the laboratory frame $$\bar{J} = \bar{\bar{\sigma}} \bar{E}. \tag{12}$$

Once the matrix of the transformation is obtained, the current density in the laboratory frame and electric fields measured in the laboratory frame can be related to the conductivities in the principle axis frame through the system of linear equations indicated by Ohm's law.

Figure 6:
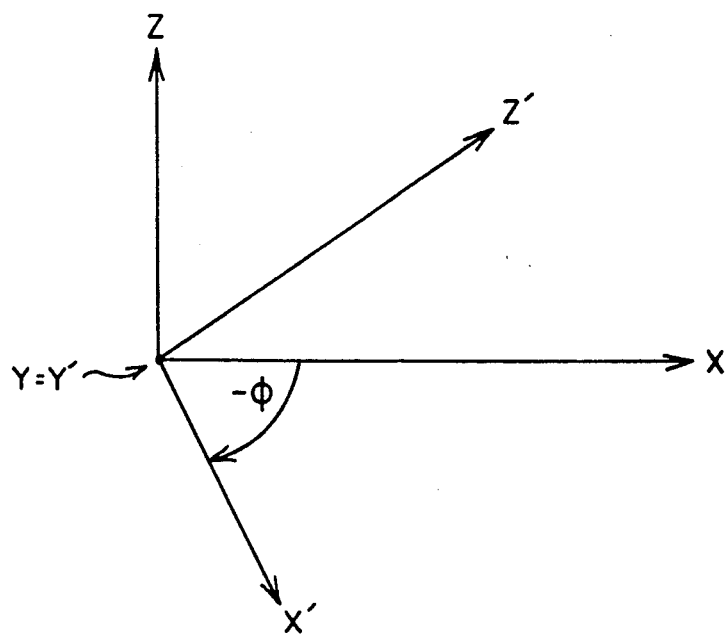
FIG. 6 illustrates the coordinate relationship of the various x, y and z coordinate directions utilized in determining the tensor conductivity components of the core sample of FIG. 5. The figure is viewed from along the y and y' axes, which coincide, and shows that the relations between the unprimed and primed coordinates is a simple rotation about the y—y' axis.

Referring to FIG. 6, unit vectors in the unprimed system $\hat{i}, \hat{j}, \hat{k}$ are related to the corresponding unit vectors in the primed system by $$\hat{i} = \hat{i}' \cos\phi - \hat{k}' \sin\phi, \tag{13}$$

$$\hat{j} = \hat{j}', \tag{14}$$

$$\hat{k} = \hat{i}' \sin\phi + \hat{k}' \cos\phi, \tag{15}$$

where $\hat{i}, \hat{j}$ and $\hat{k}$ are the customary unit vectors in the coordinate directions. In matrix form $$\begin{bmatrix} \hat{i} \\ \hat{j} \\ \hat{k} \end{bmatrix} = \begin{bmatrix} \cos\phi & 0 & -\sin\phi \\ 0 & 1 & 0 \\ \sin\phi & 0 & \cos\phi \end{bmatrix} \begin{bmatrix} \hat{i}' \\ \hat{j}' \\ \hat{k}' \end{bmatrix}, \tag{16}$$

or $\bar{u} = \bar{\bar{T}} \bar{u}'$, where $\bar{u}$ and $\bar{u}'$ are vectors whose components are the basis for their respective spaces. The transformation $\bar{\bar{T}}$ which carries $\bar{u}'$ into $\bar{u}$ carries any vector into the primed space to the corresponding vector in the unprimed space. Thus $$\bar{\bar{T}} = \begin{bmatrix} \cos\phi & 0 & -\sin\phi \\ 0 & 1 & 0 \\ \sin\phi & 0 & \cos\phi \end{bmatrix}, \tag{17}$$

and $$\bar{\bar{T}}^{-1} = \begin{bmatrix} \cos\phi & 0 & \sin\phi \\ 0 & 1 & 0 \\ -\sin\phi & 0 & \cos\phi \end{bmatrix}. \tag{18}$$

It can be verified that $\bar{\bar{T}} \bar{\bar{T}}^{-1} = \bar{\bar{I}} = \bar{\bar{T}}^{-1} \bar{\bar{T}}$. Multiplying out $\bar{J} = \bar{\bar{T}} \bar{\bar{\sigma}}' \bar{\bar{T}}^{-1} \bar{E}$ yields the matrix $$\begin{bmatrix} J_x \\ J_y \\ J_z \end{bmatrix} = \begin{bmatrix} \alpha^2 \sigma_{xx} + \beta^2 \sigma_{zz} & 0 & \alpha\beta(\sigma_{xx} - \sigma_{zz}) \\ 0 & \sigma_{yy} & 0 \\ \alpha\beta(\sigma_{xx} - \sigma_{zz}) & 0 & \beta^2 \sigma_{xx} + \alpha^2 \sigma_{zz} \end{bmatrix} \begin{bmatrix} E_x \\ E_y \\ E_z \end{bmatrix}, \tag{19}$$

where $\alpha \equiv \cos\phi$ and $\beta \equiv \sin\phi$.

With $J_y = J_z = 0$, only $J_x$ (i.e., I/A where I is injected current and A is end area of core) is injected into the core sample. Thus, multiplying out the matrix yields $$J_x = (\alpha^2 E_x + \alpha\beta E_z) \sigma_{xx} + (\beta^2 E_x - \alpha\beta E_z) \sigma_{zz}, \tag{20}$$

$$0 = \sigma_{yy} E_y, \tag{21}$$

$$0 = (\alpha\beta E_x + \beta^2 E_z) \sigma_{xx} - (\alpha\beta E_x - \alpha^2 E_z) \sigma_{zz}. \tag{22}$$

This is written in matrix form as $$\begin{bmatrix} J_x \\ 0 \\ 0 \end{bmatrix} = \begin{bmatrix} \alpha^2 E_x + \alpha\beta E_z & 0 & \beta^2 E_x - \alpha\beta E_z \\ 0 & E_y & 0 \\ \alpha\beta E_x + \beta^2 E_z & 0 & -(\alpha\beta E_x - \alpha^2 E_z) \end{bmatrix} \begin{bmatrix} \sigma_{xx} \\ \sigma_{yy} \\ \sigma_{zz} \end{bmatrix}. \tag{23}$$

From the matrix equation it can be seen that $E_y = 0$ due to the choice of orientation of the core sample.

If $\phi = 0$, $\alpha = 1$, $\beta = 0$, then from the first row of matrix $J_x = \sigma_{xx} E_x$, and from the third row of the matrix $E_z = 0$.

This is the correct limiting behaviour for the chosen orientation of the core sample. If $\phi = 90°$, $\alpha = 0$, $\beta = 1$, then $J_x = \sigma_{zz} E_x$, and $E_z = 0$, again the correct limiting behaviour.

Noting that the center row of the matrix does not contribute to the solution $$\begin{bmatrix} \sigma_{xx} \\ \sigma_{zz} \end{bmatrix} = \begin{bmatrix} \alpha^2 E_x + \alpha\beta E_z & \beta^2 E_x - \alpha\beta E_z \\ \alpha\beta E_x + \beta^2 E_z & -(\alpha\beta E_x - \alpha^2 E_z) \end{bmatrix}^{-1} \begin{bmatrix} J_x \\ 0 \end{bmatrix} \tag{24}$$

the solution of which yields the desired conductivity tensor component $\sigma_{xx}$ lying within the bedding plane and the desired conductivity tensor component $\sigma_{zz}$ normal to the bedding plane.

While the foregoing has described a preferred embodiment of the present invention, it is to be understood that various modifications or changes may be made without departing from the spirit and scope of the invention as set forth in the appended claims.

We claim:

1. A method for determining tensor conductivity components of a core sample from a transversely isotropic subterranean formation, comprising the steps of:
   a) shaping a core sample taken from a transversely isotropic subterranean formation into the form of a cylinder, having its cylindrical axis at an angle to the bedding plane of the subterranean formation comprising the core sample,
   b) applying a confining pressure to said core sample,
   c) establishing fluid saturation within said core sample,
   d) passing a current through said fluid-saturated core sample,
   e) measuring electric potential along the axial direction of said core sample,
   f) measuring electric potential in a plurality of radial directions through said core sample which are normal to the cylindrical axis of said core sample at each of a plurality of spaced-apart positions along said axis, and g) determining tensor conductivity components of said transversely isotropic formation from said measured electric potentials.

2. The method of claim 1 wherein the step of determining said tensor conductivity components comprises the determination of the tensor conductivity component normal to the bedding plane of the core sample and the determination of the tensor conductivity component lying within the bedding plane of the core sample.

3. The method of claim 2 wherein said conductivity tensor components are determined in accordance with the following $$\begin{bmatrix} \sigma_{xx} \\ \sigma_{zz} \end{bmatrix} = \begin{bmatrix} \alpha^2 E_x + \alpha\beta E_z & \beta^2 E_x - \alpha\beta E_z \\ \alpha\beta E_x + \beta^2 E_z & -(\alpha\beta E_x - \alpha^2 E_z) \end{bmatrix}^{-1} \begin{bmatrix} J_x \\ 0 \end{bmatrix},$$

where $\sigma_{xx}$ = tensor conductivity component lying within the bedding plane, $\sigma_{zz}$ = tensor conductivity component normal to the bedding plane, $E_x$ = electric vector field in the direction of the x axis, $E_z$ = electric vector field in the direction of the z axis, $J_x$ = current density vector field in the direction of the x axis, $\alpha = \cos\phi$, where $\phi$ = bedding plane angle with respect to laboratory reference frame, and $\beta = \sin\phi$.

4. The method of claim 1 further comprising the step of altering said fluid saturation within said core sample a plurality of times and repeating the conductivity and tensor conductivity component determinations for each differing fluid saturation.

5. The method of claim 4 wherein the step of altering fluid saturation comprises the step of moving the fluid in said core sample in a direction parallel to said axis.

6. The method of claim 1 wherein the step of determining tensor conductivity components comprises the steps of:

a) contacting the outer surface of said core sample with an array of electrodes at each of a plurality of spaced-apart positions along the length of said core sample, each of said arrays being in a plane normal to said axis and the electrodes in each of said arrays being equally spaced at an even number of positions about the outer surface of said core samples, b) measuring the voltage across each pair of electrodes that are spaced 180° apart about said core sample, and c) utilizing the voltage measurements across each pair of electrodes to determine the conductivity of the core sample in a radial direction through said core sample normal to said axis between said pairs of electrodes.

7. The method of claim 1 further comprising the steps of displacing at least a portion of said first fluid with a second fluid of differing electrical conductivity and repeating steps (d) to (g).

8. The method of claim 7 wherein said first fluid is electrically conductive and said second fluid is electrically non-conductive.

9. The method of claim 7 wherein said first fluid is electrically non-conductive and said second fluid is electrically conductive.

* * * * *